US007458377B2

(12) United States Patent
Falzon

(10) Patent No.: US 7,458,377 B2
(45) Date of Patent: Dec. 2, 2008

(54) METHOD AND APPARATUS FOR INTRA ORAL MYOFASCIAL TRIGGER POINT THERAPY

(75) Inventor: Gail Falzon, Ypsilanti, MI (US)

(73) Assignee: TMJ Pain Solutions, LLC, Ann Arbor, MI (US)

( * ) Notice: Subject to any disclaimer, the term of this patent is extended or adjusted under 35 U.S.C. 154(b) by 475 days.

(21) Appl. No.: 10/919,159

(22) Filed: Aug. 16, 2004

(65) Prior Publication Data

US 2005/0039760 A1 Feb. 24, 2005

Related U.S. Application Data

(60) Provisional application No. 60/496,264, filed on Aug. 19, 2003.

(51) Int. Cl.

| | |
|---|---|
| ***A61F 5/56*** | (2006.01) |
| ***A61F 5/14*** | (2006.01) |
| ***A61C 3/00*** | (2006.01) |
| ***A61B 1/32*** | (2006.01) |
| ***A61H 7/00*** | (2006.01) |
| ***A61H 31/00*** | (2006.01) |

(52) U.S. Cl. ....................... 128/861; 128/848; 128/859; 602/902; 433/141; 600/237; 601/38; 601/133; 601/134; 601/135

(58) Field of Classification Search ................. 128/848, 128/859; 602/902; 433/141; 600/237; 601/38, 601/133–135; 606/201, 204; 482/10, 11, 482/91, 148

See application file for complete search history.

(56) References Cited

U.S. PATENT DOCUMENTS

| | | | | |
|---|---|---|---|---|
| 5,577,983 | A * | 11/1996 | Fraser | 482/11 |
| 5,779,652 | A | 7/1998 | Mencher-Aliazzo | |
| 5,787,899 | A | 8/1998 | Culp | |
| 6,149,610 | A | 11/2000 | Urko | |
| 6,761,699 | B2 * | 7/2004 | Chahine | 601/135 |
| 2002/0107460 | A1 * | 8/2002 | Scheele | 601/135 |

OTHER PUBLICATIONS

Travell, Janet G. and Simons, David G., Travell & Simons' myofascial pain and dysfunction: the trigger point manual, 1983, Williams & Wilken, Baltimore, MD, p. 337, 370, 386.

* cited by examiner

*Primary Examiner*—Patricia Bianco
*Assistant Examiner*—Tarla Patel
(74) *Attorney, Agent, or Firm*—Gifford, Kruss, Sprinkle, Anderson & Citkowski, P.C.

(57) ABSTRACT

A method is provided for relief of head, face and jaw pain by achieving the release of intra oral muscle spasms, trigger points, and myofascial dysfunction. The steps include locating intra oral treatment points, including locations of intra oral muscle spasms, trigger points, and myofascial dysfunction, in the mouth and jaw region of a human subject. A handheld device is provided with a central gripping portion, a first generally arcuate arm extending from one end of the gripping portion and terminating in a generally bulbous tip, and a second generally arcuate arm extending from the other end of the gripping portion and terminating in a generally flattened tip. The subject's mouth is opened sufficiently to pass one of the tips into the mouth. One of the tips is inserted in the subject's mouth and the tip is brought into contact with one of the treatment points. Pressure is applied to the treatment point until a release response occurs.

29 Claims, 11 Drawing Sheets

FIG - 1
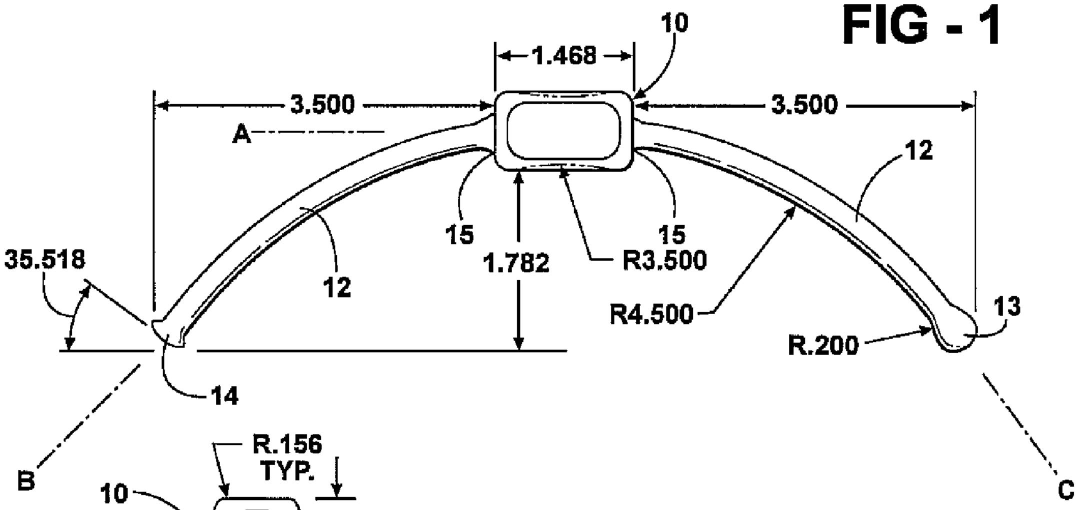
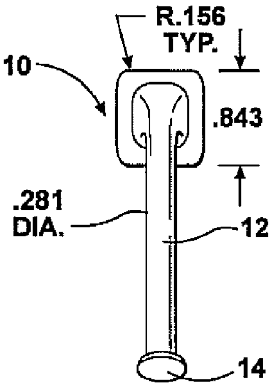
FIG - 2
FIG - 3
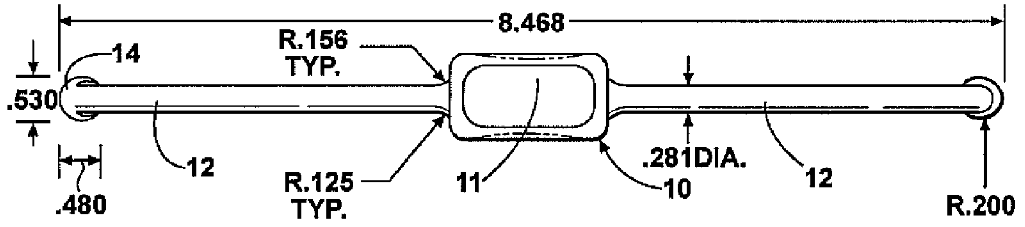
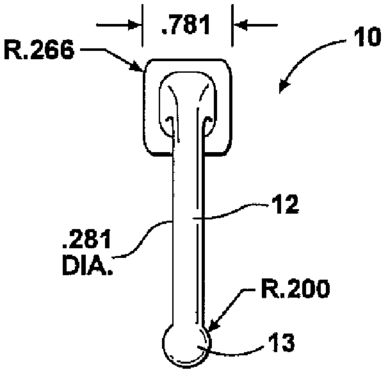
FIG - 4

FIG - 7B
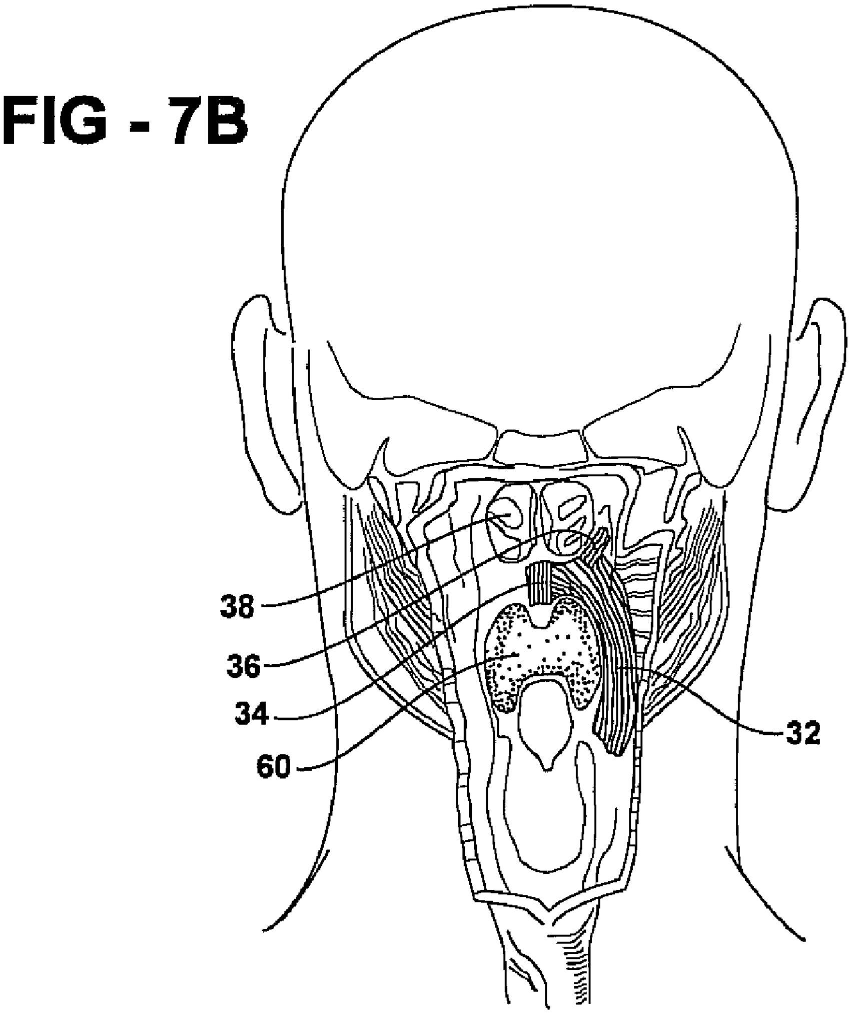
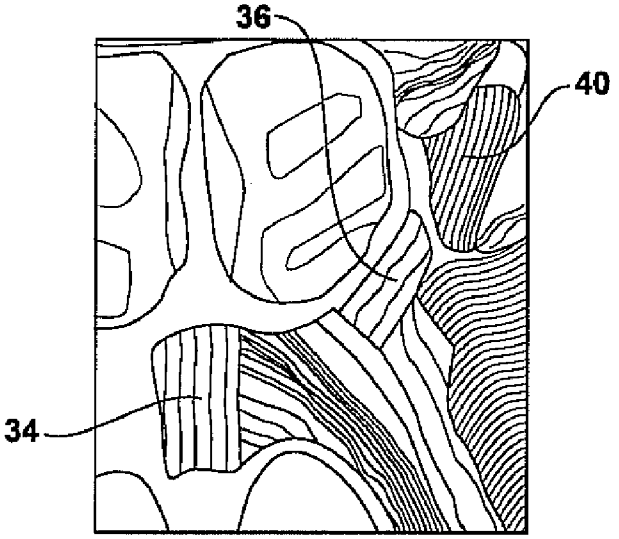
FIG - 7C

METHOD AND APPARATUS FOR INTRA ORAL MYOFASCIAL TRIGGER POINT THERAPY

REFERENCE TO RELATED APPLICATIONS

This application claims benefit of U.S. provisional patent application Ser. No. 60/496,264, filed Aug. 19, 2003, the entire content of which is incorporated herein.

FIELD OF THE INVENTION

The present invention relates to an apparatus and method for the treatment of muscular spasms, trigger points, and myofacial dysfunction located in the soft tissue within the mouth and jaw. More particularly, the present invention relates to an apparatus and method for the treatment of muscular spasms, trigger points, and myofacial dysfunction located in the soft tissue within the mouth and jaw associated with head, face, and jaw pain, including Temporomandibular Joint Disorder (known as "TMJ").

BACKGROUND OF THE INVENTION

In the medical field of muscular and myofacial pain, Dr. Janet Travell is recognized as the leading pioneer. She began her work in the 1940s, in the United States. She developed an entire branch of medicine, known as "Myofacial Therapy". She was President John F. Kennedy's personal physician, and successfully treated his chronic back condition. Myofacial trigger point therapy is based almost entirely on Dr. Travell's work, and is the most effective modality used today by clinicians and therapists who treat muscular and myofacial dysfunction and pain. It is a therapeutic technique that involves the systematic application of pressure to tender muscles and myofacial tissue in order to relieve pain and dysfunction.

Myofacial tissue (also called "fascia") wraps around muscle tissue, muscle fibers, bundles of fibers, and the muscles themselves. It then continues on to form tendons and ligaments. Thus, fascia and muscle tissues are interwoven. When muscles and fascia are in their normal, relaxed state, the layers of facial tissue, muscle fibers, bundles of fibers, and the muscles themselves all glide alongside one another. When muscular dysfunction is present, muscles contract (cramp) to varying degrees, which is known as "going into spasm". Moreover, facial dysfunction always arises from muscular dysfunction.

Ordinary muscle cramps and contractions release with movement, that is, stretching of the affected musculature. When the muscle is locked into a deep and painful spasm, it forms a "trigger point." (Another term commonly used instead of trigger point is "contraction knot.") Trigger points do not release with movement (stretching). Instead, they are locked into a strong state of contraction. This contraction is essentially a localized hardening of the muscle tissue and associated fascia.

Once the muscle and fascia tissues harden, they become "frozen" in that state. The fascia also forms adhesions, which further restrict the muscle from moving due to a "shrinking" (constriction) effect. Stretching these hardened tissues usually results in a deeper spasm, as the muscle and fascia attempt to protect themselves from what they perceive as further injury. Thus, trigger points require specialized treatment, known as trigger point therapy, to return to their normal, relaxed states.

When a muscle spasms, it sends a message to the nervous system, which in turn causes an even greater contraction, which causes more pain, and so forth. Muscles work in opposing pairs, so when one muscle spasms, the opposing muscle will often spasm in response. Thus, a singular muscle spasm (trigger point) can send a chain reaction of spasm that affects several parts of the body.

The network of nerves in the body passes through the muscular system. When a muscle develops a trigger point (goes in spasm), it compresses the nerve, which sends a message of pain to the brain. Since nerves can pass through many muscles, sometimes the pain is felt in a muscle other than the originating site. This phenomenon is known as "referred pain." Trigger points regularly cause referred pain. One muscle can have more than one trigger point and associated myofacial dysfunction and constriction.

Trigger point therapy is the application of sustained, direct pressure onto a trigger point. It is most beneficial if this pressure can be repeatedly applied, and at different angles. This pressure interrupts the neural signals that cause both the spasm and the pain. It ultimately lengthens the muscle into its normal state, which effectively breaks the spasm-pain-spasm cycle as well as referred pain. It also enables the myofacial tissue to release any constriction, and return to its normal state.

Trigger point therapy is well known and widely used in the medical field on the muscles of the body, for example, the back or shoulder. In the case of TMJ and other head, face, and jaw pain, if trigger point therapy is used, it is almost always used on the muscles located outside of the mouth. However, the trigger points that are responsible for TMJ and other head, face, and jaw pain, are located inside the mouth. Thus, extra oral trigger point therapy is insufficient, inappropriate, and an ineffective means of treatment.

Clinicians rarely, if ever, utilize treatment of trigger points inside the mouth and jaw. The handful of those that do employ intra oral trigger point therapy use their fingers because there are no available tools on the market. Using one's fingers is a limiting factor because of their size (too big) and length (too short), which makes them unsuitable relative to the tasks of inserting and manipulating them within a patient's mouth to release trigger points. Painful and invasive techniques to release intra oral trigger points are the clinical norm, such as needle injection therapy (including but not limited to cortisone, anesthetic, and dry needle), or medication therapy (including but not limited to muscle relaxants, anti-anxiety, anti-depressants, anti-inflammatories, and pain relievers).

There are many tools on the market designed for the treatment of trigger points located on the "outside" of the body. Many of these tools are unusually shaped, for example, like a spider; the tool has a main spherically shaped body and several different curvy and/or arched "legs". These tools generally cannot fit into a human mouth. If a patient had adequate jaw mobility and could open the jaw very wide, these tools might fit, but the entire tool would have to be inserted, as the "leg" length is rather short with various curvatures. The patient would most likely end up with their jaw lodged open, and might gag. If these tools were made smaller so they could fit comfortably into a human mouth, their shape and size would still prohibit them from being functionally useful to release intra oral muscle spasms, trigger points, and myofacial dysfunction, as they are designed for use on the outer body of a human.

There are also other tools on the market designed for massaging the body, such as tools shaped like dolphins, small rolling pins, or miniature rodents. They are usually quite thick and wide. Again, while a patient might be able to fit one of these into his or her mouth, the dimensions of the tool are inappropriate for proper manipulation and operability to treat intra oral trigger points. The patient would likely also end up with their jaw lodged open as with the above-mentioned tools. There is also a body massage tool shaped like a large question mark, which is designed specifically so one can hook the curved part of the "question mark" over his or her shoulder, and massage the upper back. The ends of this tool could fit into a human's mouth, but the end caps are about the size of large gumballs, which are too large to be used for intra oral trigger points. Additionally, the shape and overall curvature of this tool do not allow for proper manipulation and operability to treat intra oral trigger points. Lastly, it would most likely result in tremendous discomfort to the human on the receiving end of the treatment.

Lastly, if a massage tool is straight, even if it slim in diameter like a writing utensil, the lack of curvature makes it basically impossible to connect with the vast majority of intra oral trigger points. A straight or minimally curved tool would hit approximately less than 10% of intra oral trigger points, muscle spasms, and locations of myofacial dysfunction. One would also have to open his/her jaw very wide to use a straight tool. Many patients with head, face, and jaw pain have restricted jaw mobility and cannot open their jaws more than one or two fingers' width. Additionally, there are many intra oral trigger points located deep within the mouth. Straight tools would touch other portions of the mouth and jaw while making contact with the trigger points, which can range from uncomfortable to painful, can activate the gag reflex, and can possibly damage delicate tissues.

Therefore, there is a need for a non-invasive, effective, easy to use, drug free and pain free apparatus and method for the treatment of muscular spasms, trigger points, and myofacial dysfunction located in the soft tissue within the mouth and jaw associated with head, face, and jaw pain, including TMJ. Approximately 15% to 20% of the general population suffers from TMJ alone. The percentage is higher for those suffering from other types of head, face, and jaw pain.

SUMMARY OF THE INVENTION

The present invention relates to an apparatus and method for the treatment of muscular spasms, trigger points, and myofacial dysfunction located in the soft tissue within the mouth and jaw associated with head, face, and jaw pain, including TMJ.

The method includes the steps of locating intra oral treatment points selected from the group consisting of locations of intra oral muscle spasms, trigger points and myofacial dysfunction in the mouth and jaw region of a human subject. A handheld device is provided that comprises a central gripping portion having a pair of spaced-apart ends. A first generally arcuate arm extends from one end of the central gripping portion and terminates in a generally bulbous tip. A second generally arcuate arm extends from the other end of the central gripping portion and terminates in a generally flattened tip. Further steps of the method include opening the subject's mouth sufficiently to pass one of the tips into the mouth. One of the tips is inserted into the subject's mouth and is brought into contact with one of the treatment points. Pressure is applied to the treatment point until a release response occurs.

The apparatus aspect of the present invention provides a handheld device for insertion into the mouth of a human and for use in the release and relief of muscular spasms, trigger points, and myofacial dysfunction through the systematic application of pressure. The device includes a central gripping portion having a pair of opposed ends and a plurality of gripping faces extending between the opposed ends. A first generally arcuate arm extends from one of the opposed ends. The arm has a base joined to the end and a tip space therefrom, with an elongated mid-portion extending generally accurately therebetween. The tip is generally bulbous and convex with a radius of curvature between 0.15 and 0.4 inches and a width between 0.25 and 0.6 inches. A second generally arcuate arm extends from the other end of the central gripping portion. The second arm has a base joined to the gripping portion and a tip spaced therefrom, with an elongated mid-portion extending generally accurately therebetween. The tip has a face that is generally flattened with the width between 0.2 and 0.9 inches. Further advantages of this invention will become apparent from a consideration of the drawings and ensuing description.

BRIEF DESCRIPTION OF THE DRAWINGS

FIG. 1 is a side elevational view of one embodiment of a device according to the present invention;

FIG. 2 is an end view of the device of FIG. 1;

FIG. 3 is a top view of the device of FIG. 1;

FIG. 4 is an opposite end view of the device of FIG. 1;

FIG. 7B is a posterior view of a human head illustrating the palatopharyngeus and levator veli palatini muscles;

FIG. 7C is a posterior view of a human head illustrating the tensor velipalatini, levator veli palatini, and inner insertions of the pterygoid muscles;

DETAILED DESCRIPTION OF THE INVENTION

Figure 5:
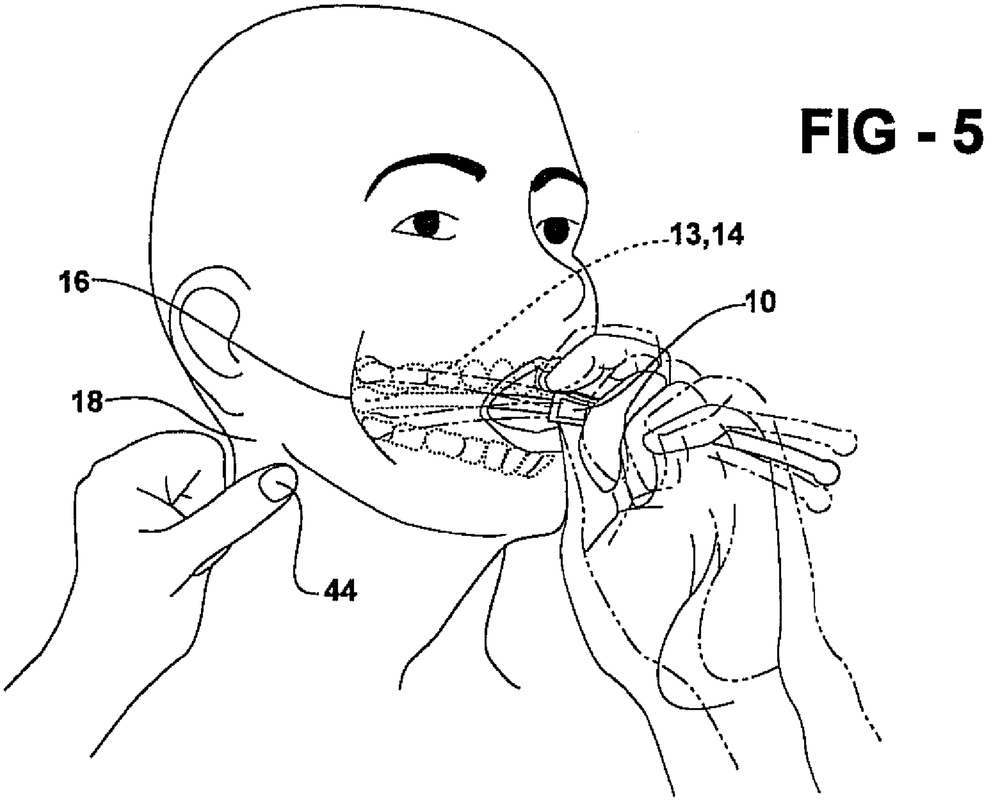
FIG. 5 is a perspective view of a human head illustrating a method according to one aspect of the present invention for achieving release and relief of intra oral muscular spasms, trigger points, and myofacial dysfunction specifically in the area around and within the medial pterygoid and buccinator muscles.

The present invention will be described with regard to the accompanying drawings that assist in illustrating various features of the patent. In this regard, the present invention generally relates to an apparatus and method for the treatment of muscular spasms, trigger points, and myofacial dysfunction located in the soft tissue within the mouth and jaw associated with head, face, and jaw pain, including TMJ.

A particular embodiment of a device for the treatment of intra oral muscular spasms, trigger points, and myofacial dysfunction is illustrated in FIGS. 1-4. The device includes a central gripping portion 10 and a pair of elongated arms 12 where each arm 12 terminates in a different shaped tip 13, 14. The gripping portion 10 has a pair of opposed ends 15 with a plurality of gripping faces 11 extending between the ends. The arms 12 each extend from one of the ends 15 and are preferably integrally formed with the gripping portion 10 so as to function in combination as a single unit. The device can be used by a human being whereby a human can insert the device into the mouth of a human to apply a sustained, systematic application of pressure to intra oral trigger points, muscle spasms, and myofacial dysfunction.

The entire device is preferably about 8.5 inches long and crescent-shaped. The gripping portion 10 is preferably rectangular with a generally square cross section and has concave thumb and/or finger indentations 11 on all four sides. The preferred approximate dimensions are 1.468 inches in length, 0.843 inches in height, and 0.781 inches in width, as shown in the Figures. The dimensions given in the Figures are for one preferred embodiment but do not limit the invention to those dimensions. The gripping portion 10 is large enough to ensure a comfortable, sure grip, and easy handling. If it were substantially different in size or shape, the device would likely become awkward to handle. The surface of the entire device, including the terminal ends 13, 14, 15 is preferably smooth and without seams, so as to not catch, snag or cut any tissue within the mouth. In one preferred approach, the device is formed from a core made of a relatively rigid and strong plastic, metal, or reinforced plastic, and the core is partially or fully coated with a second material that is softer and seamless. One preferred coating is an FDA approved and/or food grade PVC that has a somewhat rubbery feel.

The arms are preferably generally arcuate extensions 12 that protrude from either end 15 of the gripping portion 10, with each having a preferred length of about 3.5 inches. While the arms could be longer or shorter, such as in the range of 3 to 6 inches, the approximate 3.5 inch length is preferred because it is long enough to reach the various treatment locations and not so long as to be unwieldy. As another alternative, the arms could have different lengths than each other. Each arm 12 has a base joined to the gripping portion 10 and terminates in a tip or blunt end 13, 14. The arms may be said to have a midportion that extends between the base and tip, with the midportion preferably being arcuate and having a preferred diameter of about 0.281 inches and preferred radius of curvature of about 4.5 inches. Again, other dimensions are possible, such as the midportion having a diameter in the range of 0.25 to 0.6 inches and the radius of curvature being in the range of 4 to 5 inches, or even 3 to 6 inches, but the stated dimensions are preferred. These dimensions provide improved functionality. Alternatively, the two arms could have different diameters and radii of curvature than each other. The tip 13 of one arm 12 is preferably round and smooth like a sphere, and has a preferred radius of curvature of 0.2 inches and a preferred width of about 0.3 inches. The tip 13 could have a radius of curvature as small as 0.15 inches up to 0.25 inches, or in some cases up to 0.4 inches, and a width in the range of about 0.25 to about 0.625 inches, but 0.2 inches and 0.3 inches, respectively, are preferred, as these dimensions provide a good size for treatment. The opposite tip 14 is preferably smooth and somewhat flat like a convex version of a golf tee, with a preferred diameter of about 0.5 inches. The tip 14 could have a width in the range of 0.25 to 0.9 inches, but 0.5 is preferred, as a good size for treatment. It is preferred that the convex face of the tip 14 have a radius of curvature greater than the radius of curvature of the tip 13. Also, it is preferred that the tip 14 be wider than the tip 13.

The specific angle and curvature of the arms 12 was adapted because the direction of pressure must be applied at certain angles to achieve maximum treatment benefit. This design not only enables users to apply pressure at these angles, but also to attain contact with hard-to-reach trigger points within the mouth. The diameter of the arms 12 must be small enough to fit into the mouth without requiring the jaw to be open very wide, because many patients requiring treatment are unable to open the mouth more than one to two fingers' width between the teeth.

The tips may be angled at various angles relative to the grip. Referring to FIG. 1, a grip axis A may be defined as axially extending through the gripping portion 10. A tip axis may be defined as extending axial through each tip and through the end face, as shown at B and C. A tip angle may be defined for each tip as the angle between the grip axis A and the tip axis B or C. It is preferred that the tip axes be in the range of 20 to 60 degrees, with 30 to 50 degrees being more preferred, and about 35 to 45 degrees being most preferred.

The length of the arms 12 is made long enough to easily reach all of the possible trigger points within the mouth. Any substantial increase in length would make the device too long and cumbersome. The device is rigid enough to apply the appropriate amount of pressure but soft enough to diminish the risk of bruising or tissue damage. As shown in FIGS. 1-4, the preferred width of the arms 12 is about 0.25 inches, although the width could vary from 0.15 to 0.28. It is also preferred that the diameter of the arms 12 be smaller than the diameter of the tips 13,14.

The locations of intra oral musculature origins and insertions also suffer from trigger points. They are exceptionally difficult to reach. Various intra oral anatomical notches and grooves are also difficult to reach. Each tip's surface is specifically designed to best reach and fit into these origins, insertions, notches, and grooves, as well as comfortably apply pressure to them. If the tips were made a substantially different size or shape, they would not function properly, effectively decreasing therapeutic treatment.

Overall, the design of the device makes the treatment of trigger points, muscle spasms, and myofacial dysfunction very easy and highly effective. The device may be operated by a human to treat her or himself, or may be operated by one individual to treat another.

As will be clear to those of skill in the art, the device may be altered in various ways without departing from the teaching of the present invention. For example, a device could be made with only one arm, rather than two. Also, the arms could lie in different planes. However, the illustrated embodiment is preferred.

Another aspect of the present invention is a method of using the device as described herein, and shown in FIGS. 5-9D. The method is for achieving release and relief of intra oral muscular spasms, trigger points, and myofacial dysfunction and preferably includes the steps of the touching one of the tips 13, 14 to intra oral muscle spasms, trigger points, and myofacial dysfunction and applying sustained pressure on the arm 12, possibly at numerous and dissimilar angles in an amount sufficient to elicit release and relief.

The preferred method generally starts with identifying intra oral treatment points, which are defined as locations of intra oral muscle spasms, trigger points and myofacial dysfunction. One type of treatment point is an active myofacial trigger point, which may be defined as a myofacial trigger point that causes a clinical pain complaint. It is always tender, prevents full lengthening of the muscle, weakens the muscle, refers pain,, and/or mediates a local twitch response of muscle fibers when palpated. If these active trigger points are not treated, blood vessels and nerves become entrapped in the muscle and myofacial tissue, and can cause debilitating pain as well as lead to permanent tissue damage. The locations where treatment points will be found include areas of various jaw and head muscles, accessible intra orally. The various locations where some treatment points are found will be described with reference to the Figures. Once one or more treatment points are located, they are treated using the device described previously. The subject's mouth is opened sufficiently to pass one of the tips into the mouth, and the tip is brought into contact with one of the treatment points. Then, pressure is applied to the treatment point until a release response occurs.

Figure 5A:
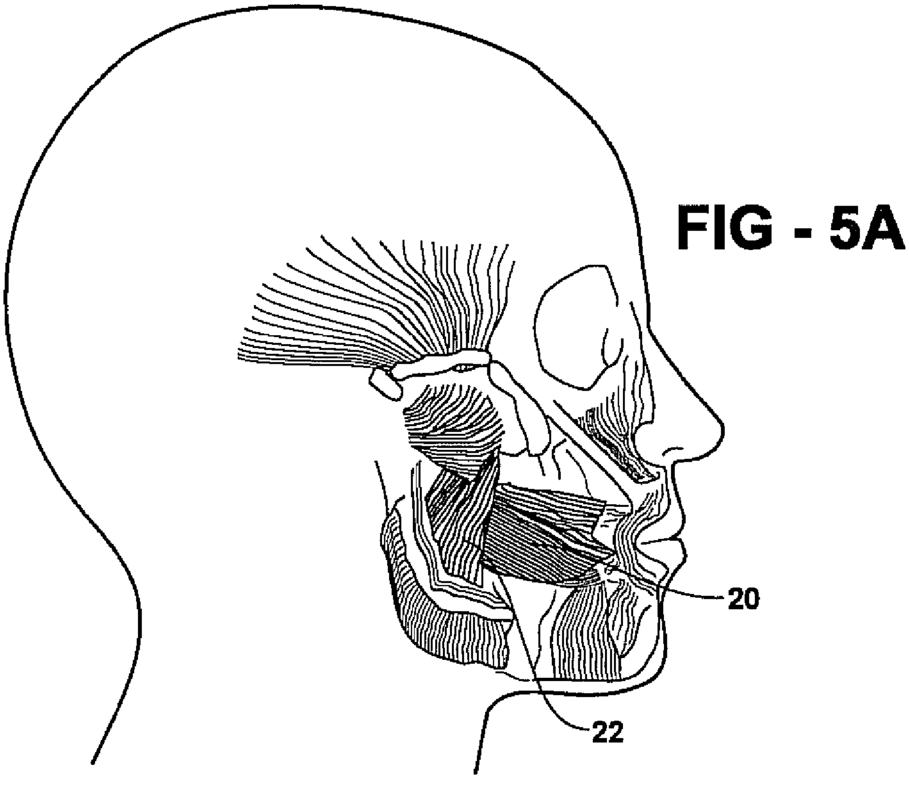
FIG. 5A is a side view of a human head illustrating the medial pterygoid and buccinator muscles.
Figure 5B:
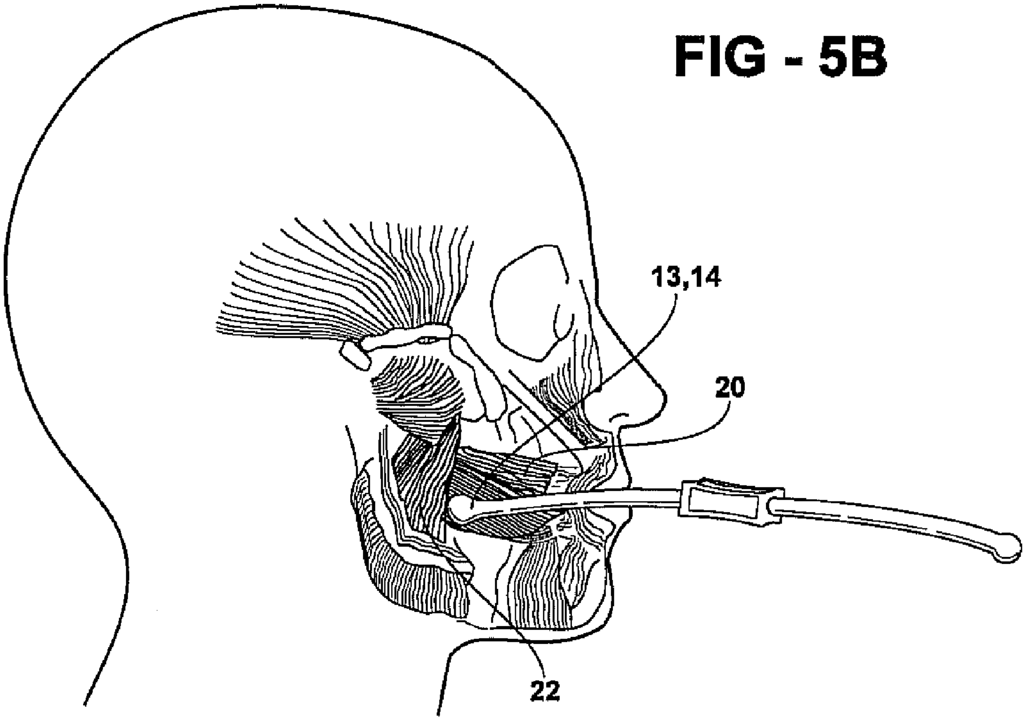
FIG. 5B is a side view similar to FIG. 5A with a device according to one embodiment of the present invention positioned for treatment.

FIG. 5 illustrates a method according to one aspect of the present invention for achieving release and relief of intra oral muscular spasms, trigger points, and myofacial dysfunction, specifically in the area around and within the medial pterygoid 22 and buccinator 20 muscles, shown in FIG. 5A and FIG. 5B. To begin treatment of a human's intra oral trigger points, the human must start with a slightly parted, relaxed mouth, as shown in FIG. 5. The two rows of teeth inside the mouth also should be slightly apart, up to about one half of one inch. The human can receive treatment sitting in an upright position, but it is preferred that the human is positioned in a reclined position to 45 degrees with the head resting on some type of support, such as a head rest in a dental chair or on a pillow. Treatment can begin on either side of the mouth. When treatment of one side concludes, begin treatment of the other side. The gripping portion 10 is initially held so that the device is positioned generally horizontally (assuming the upper jaw is also horizontal). A plane may be defined as vertically bisecting the subject's head into a right and left half, with the plane passing through the subject's nose. The device is positioned with one tip in the mouth and one tip outside the mouth, and the outside tip is curved away from the plane. Stated another way, the center of curvature of the device is on the outboard side of the device with respect to the plane. If the device is being used to treat the right side of the head, as shown in FIG. 5, the outside tip will curve to the right. The gripping portion 10 will end up positioned slightly to the side of the mouth on the same side as is being treated. One of the tips 13, 14 is guided into the soft tissue area 16 between the top and bottom molars, as shown in FIG. 5 and FIG. 5B. This causes the tip to contact the medial pterygoid muscle. It should be noted that FIG. 5B illustrates the tip 13, 14 such that it may appear to be outboard of the buccinator. The tip and the midportion is inboard of the buccinator, which is partially in the cheek. The midportion and the tip extend inboard of the cheek. The tips 13, 14 of the device may be said to be pointed in a direction. For the procedure illustrated in FIGS. 5 and 5B, the tip in the mouth is pointed rearwardly with respect to the head. It may be moved or angled upwardly and downwardly to contact different portions of the medial pterygoid muscle. The tip is used to locate the first area of tenderness (the first treatment point) and is placed so that it makes contact with the area 16. The user should begin to apply pressure by pushing the tip rearwardly and toward the ear on the same side of the head.

The following approach to applying pressure preferably applies to all aspects of the present invention discussed herein. The user should apply sustained pressure to only one area at a time, in an amount sufficient to elicit release and relief. To achieve release and relief, the user should start with a small to moderate amount of pressure. The correct amount of pressure will first result in mild to moderate discomfort. The correct amount of pressure varies from trigger point to trigger point. The correct length of time for sustained pressure also varies from trigger point to trigger point. A timed method can be used, such as holding the pressure for a length of 15 to 30 seconds, then releasing the pressure, then repeating several times. A more sophisticated and comprehensive approach involves holding the sustained pressure until the trigger point releases. This is referred to herein as a release response and manifests as different behaviors of the trigger point muscle fibers and myofacial tissue. Examples include, but are not limited to, feeling like the area in contact with the tip softens or "melts, either slowly or suddenly. Or, the treatment point may feel like it "gives way", either slowly or suddenly. The release response may also feel like the area in contact with the tip shifts or jumps, either slowly or suddenly. The discomfort may elevate slightly or to a greater extent, then either decrease slightly or to a greater extent, or dissipate completely. Once the trigger point releases, the user should disengage contact between the tip and the trigger point. It is optional to allow for one to a few moment(s) of rest time before re-initiating contact and re-application of sustained pressure. If application of a greater amount of pressure does not result in more than moderate discomfort, then it is appropriate to use the greater amount of pressure. This step may need to be repeated several times with increasing pressure to achieve full release and relief. Once release and relief is achieved, move to the next area of tenderness.

For maximum benefit in the method illustrated in FIGS. 5 and 5B, the operator of the device may place his or her thumb 44 of the free hand on the outside of the cheek slightly below the curve of the jawbone 18 closest to the ear, and apply pressure with the thumb 44 at the same time the device applies pressure by pushing the thumb 44 toward the opposite side of the head, as shown in FIG. 5. Those on the receiving end of treatment may find variations in preference with regard to blunt end selection per area of tenderness per application of sustained pressure. It is highly important for those on the receiving end of treatment according to any aspect of the present invention to maintain an even, steady breathing pattern and to stay as relaxed as possible during treatment.

Figure 6:
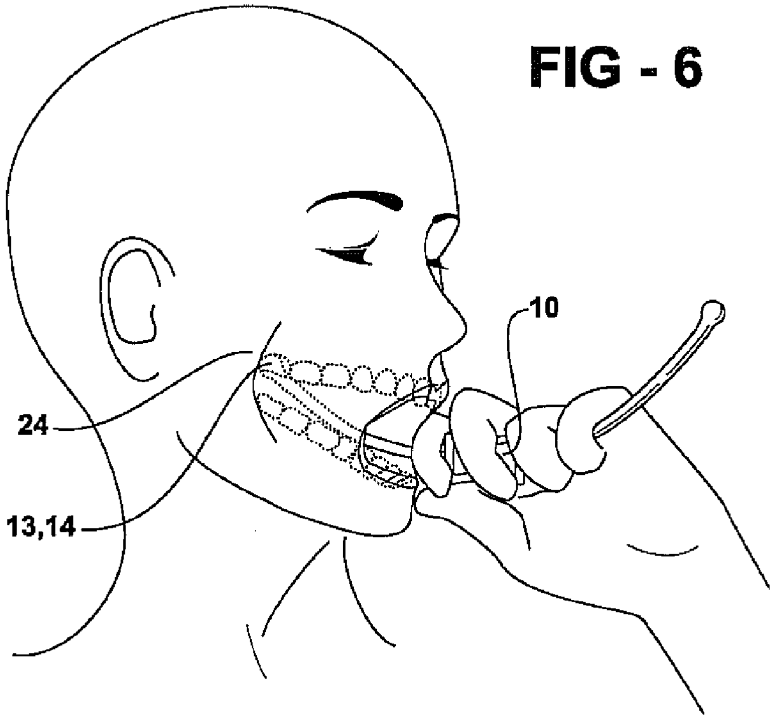
FIG. 6 is a perspective view of a human head illustrating a method according to another aspect of the present invention for achieving release and relief of intra oral muscular spasms, trigger points, and myofacial dysfunction specifically in the area around and within the lateral pterygoid muscle.
Figure 6A:
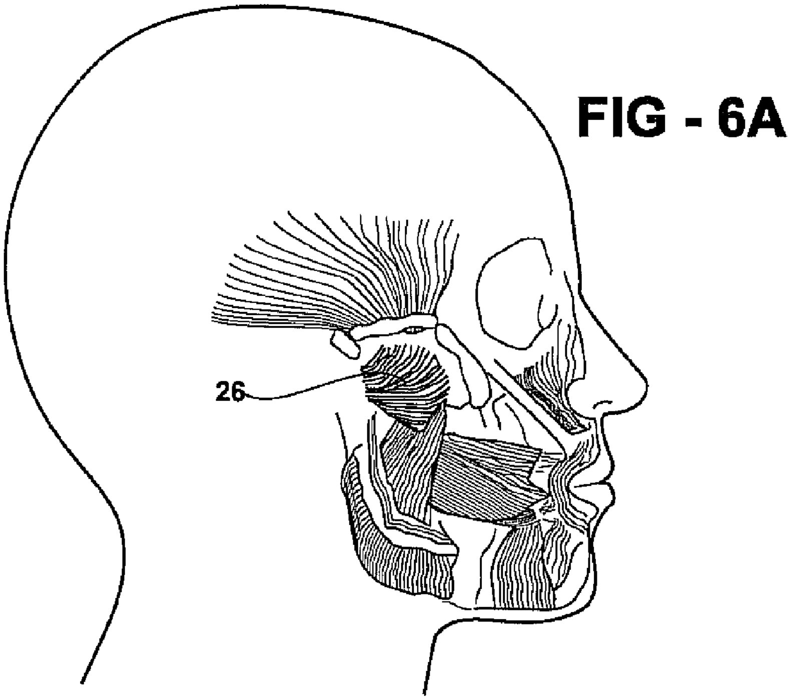
FIG. 6A is a side view of a human head illustrating the lateral pterygoid muscle.
Figure 6B:
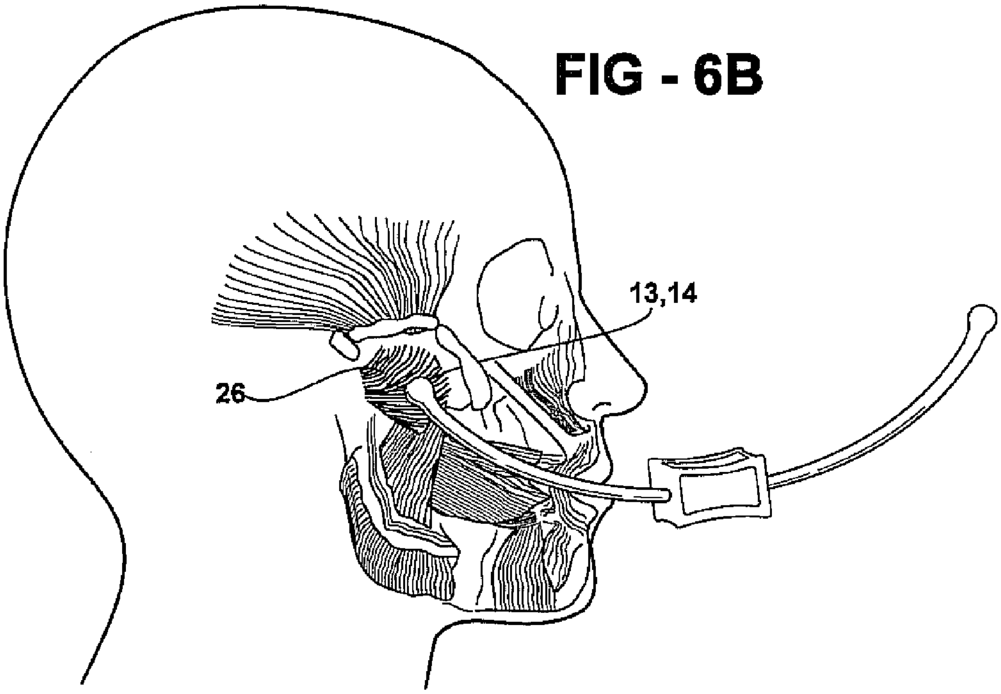
FIG. 6B is a side view similar to FIG. 6A with a device according to one embodiment of the present invention positioned for treatment.

FIG. 6 illustrates a method according to another aspect of the present invention for achieving release and relief of intra oral muscular spasms, trigger points, and myofacial dysfunction, specifically in the area around and within the lateral pterygoid muscle 26, shown in FIG. 6A and FIG. 6B. To begin treatment of the subject's intra oral trigger points, the subject must start with a slightly parted, relaxed mouth. The two rows of teeth inside the mouth also should be slightly apart, up to about one half of one inch. The human can receive treatment sitting in an upright position, but it is preferred that the human is positioned in a reclined position to 45 degrees with the head resting on some type of support, such as a head rest in a dental chair or on a pillow. Treatment can begin on either side of the mouth. When treatment of one side concludes, begin treatment of the other side. The gripping portion should initially be held such that the device is positioned generally in a vertical plane, as shown in FIG. 6. The tips 13, 14 should be pointing up. The user should guide either tip of the device into the area behind and slightly outside of the upper molars 24 as shown in FIG. 6. The correct area will feel like an indentation behind the upper molars. The area 24 is not directly behind the upper molars. The area 24 is located slightly toward the outside of the molars. The size of the indentation may vary from subject to subject and also may vary depending on the amount and severity of trigger points in this area. The user should locate the first area of tenderness and place the tip 13, 14 so that it makes contact with the area 24. The user should begin to apply pressure by pushing generally straight up. The application of pressure to achieve a release response was discussed with respect to FIGS. 5-5B and applies here as well.

Figure 7:
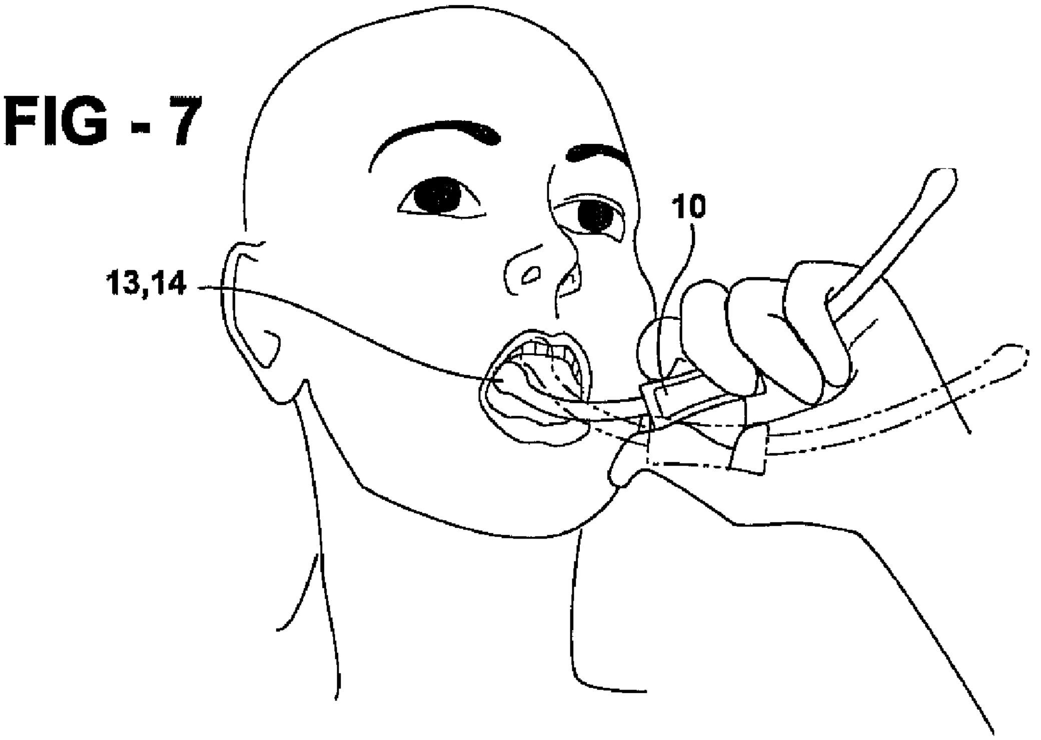
FIG. 7 is a perspective view of a human head illustrating a method according to an additional aspect of the present invention for achieving release and relief of intra oral muscular spasms, trigger points, and myofacial dysfunction specifically in the area around and within the palatopharyngeus, tensor veli palatini and levator veli palatini muscles as well as the area around and within the portion of both pterygoids located closest to the roof of the mouth.
Figure 7A:
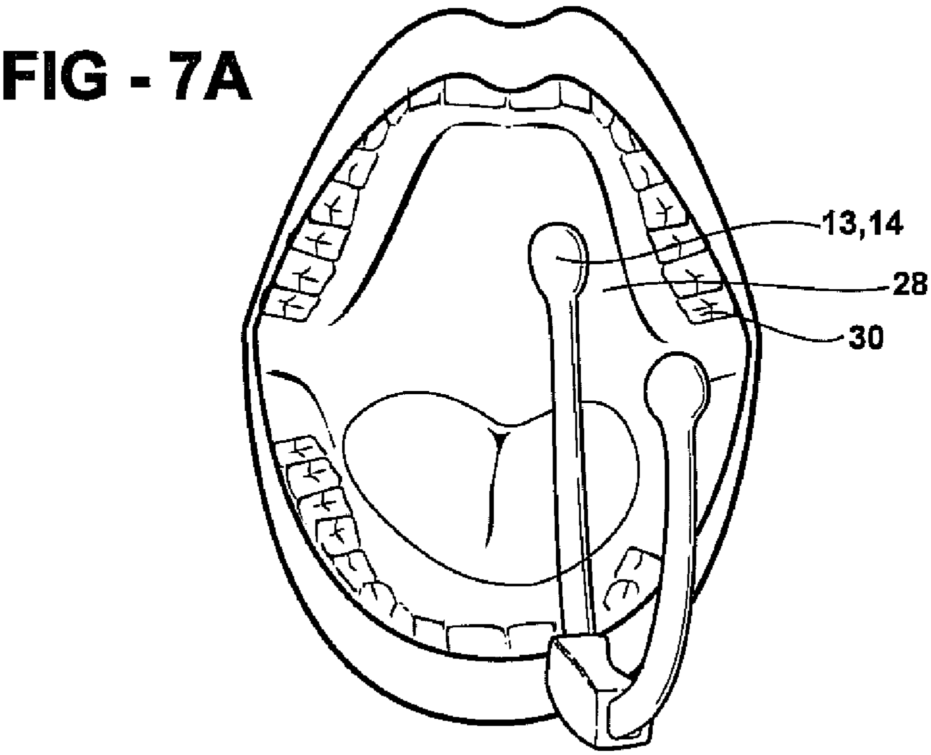
FIG. 7A is a front view of a human mouth illustrating a method according to the additional aspect of the present invention for achieving release and relief of intra oral muscular spasms, trigger points, and myofacial dysfunction specifically in the area around and within the palatopharyngeus, tensor veli palatini, and levator veli palatini muscles as well as the area around and within the portion of both pterygoids located closest to the roof of the mouth.

FIG. 7 illustrates a method according to a further aspect of the present invention for achieving release and relief of intra oral muscular spasms, trigger points, and myofacial dysfunction, specifically in the area around and within the palatopharyngeus 32, tensor veli palatini 40, and levator veli palatini 36 muscles as well as the area around and within the portion of the pterygoids 22, 26 located closest to the roof of the mouth 28, shown in FIG. 7A, FIG. 7B and FIG. 7C. As with the prior methods, the subject should start with a slightly parted, relaxed mouth and two rows of teeth inside the mouth also should be slightly apart, up to about one half of one inch. For this treatment, it is preferred that the subject opens the mouth a greater distance than one half of one inch, up to approximately two inches. For those unable to open to this distance, the opening of one half of one inch shall suffice. The subject can receive treatment sitting in an upright position, but it is preferred that the subject is positioned in a reclined position to 45 degrees with the head resting on some type of support, such as a head rest in a dental chair or on a pillow. If the subject is receiving treatment in a seated, upright position, it is preferred to have the subject lift his or her chin two to three inches before treatment commences. Treatment can begin on either side of the mouth. When treatment of one side concludes, begin treatment of the other side. The gripping portion 10 should be held such that the device is positioned generally in a vertical plane, as shown in FIG. 7. The midportion of the elongated arm should point down so that the tips 13, 14 are pointing up. The user should guide either tip of the device into the mouth, inside the top row of teeth, until the device is positioned behind the last tooth 30, as shown in FIG. 7A. The user should move the tip slowly toward the soft palate 28 as well as slightly toward the rear of the mouth. As soon as the terminal end passes over the bony prominences, located on the inside of the top row of the teeth, the terminal end will "sink" into the soft palate 28, as shown in FIG. 7A. FIG. 7B shows the muscles that extend through the soft palate 28. These muscles include the palatopharyngeus 32, tensor veli palatini 40, levator veli palatini 36, and the inside portion of the pterygoids 22, 26. These muscles in the soft palate area form a "floor" under the sinus cavity. The sinus cavity is above this "floor" of muscles, and next to the nasal cavity 38, shown in FIG. 7B. Trigger points and myofacial dysfunction will be located throughout these muscles. It is best to start treatment where the terminal end "sinks" into the soft palate 28 as described earlier and move toward the muscle of the uvula 34, shown in FIG. 7B, in order to avoid activating the gag reflex, which can easily happen if the treatment is started closest to the muscle of the uvula 34. Once the first area of tenderness is located, the user should place the tip 13, 14 so that it makes contact with the area. The user should begin to apply pressure by pushing up and slightly angled toward the crown of the head. The user should apply sustained pressure to only one area at a time, in an amount sufficient to elicit release and relief, as discussed previously.

Figure 8:
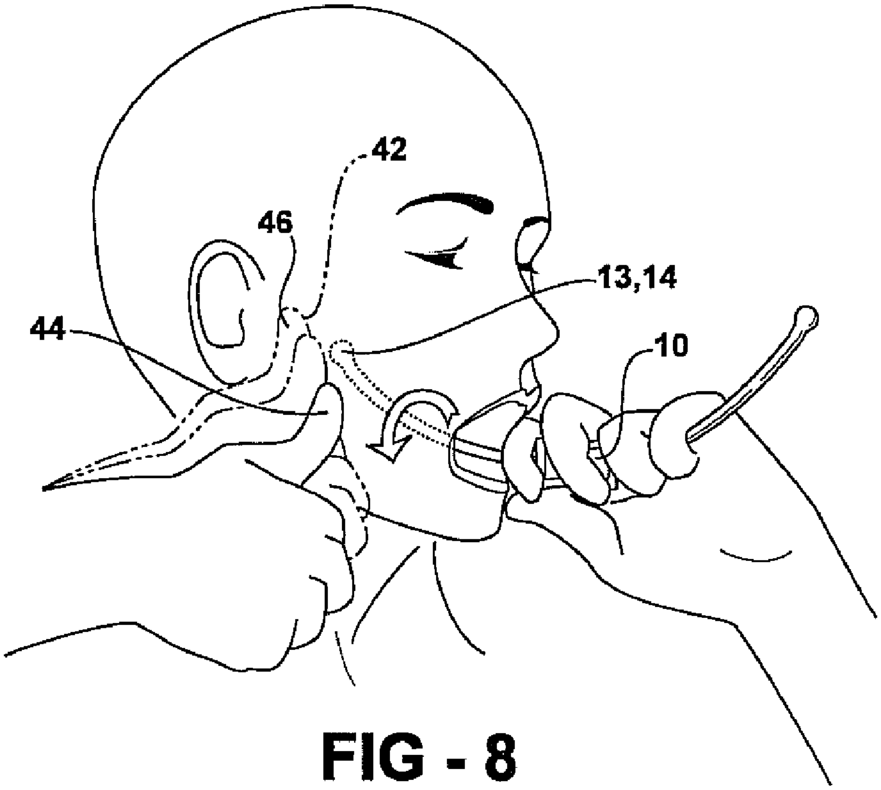
FIG. 8 is a perspective view of a human head illustrating a method according to a further aspect of the present invention for achieving release and relief of intra oral muscular spasms, trigger points, and myofacial dysfunction specifically in the area around and within the masseter, buccinator, stylopharyngeus, middle pharyngeal constrictor, and superior pharyngeal constrictor muscles.
Figure 8A:
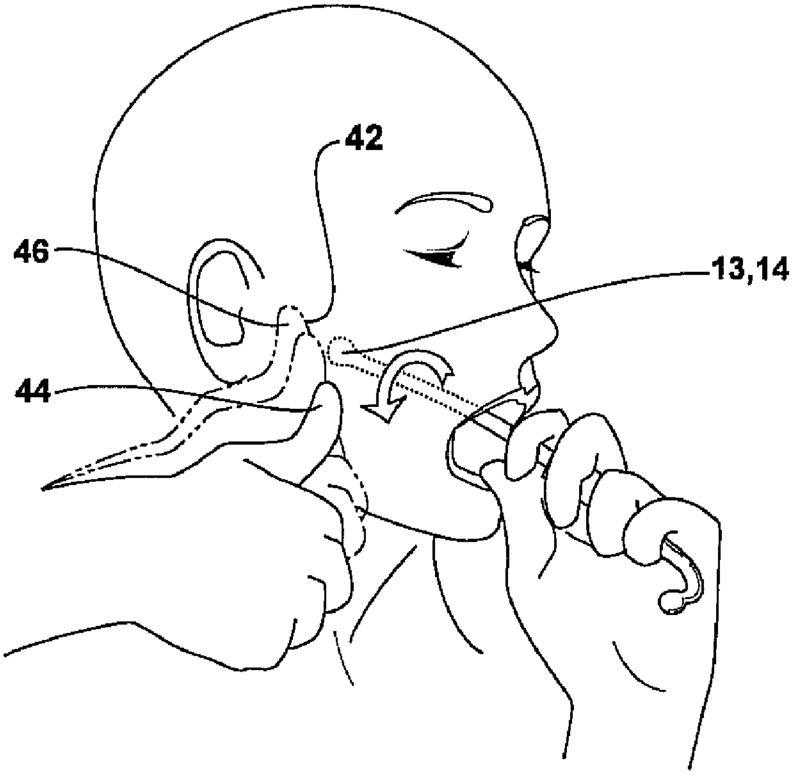
FIG. 8A is a view similar to FIG. 8, with the treatment device repositioned for further treatment.
Figure 8B:
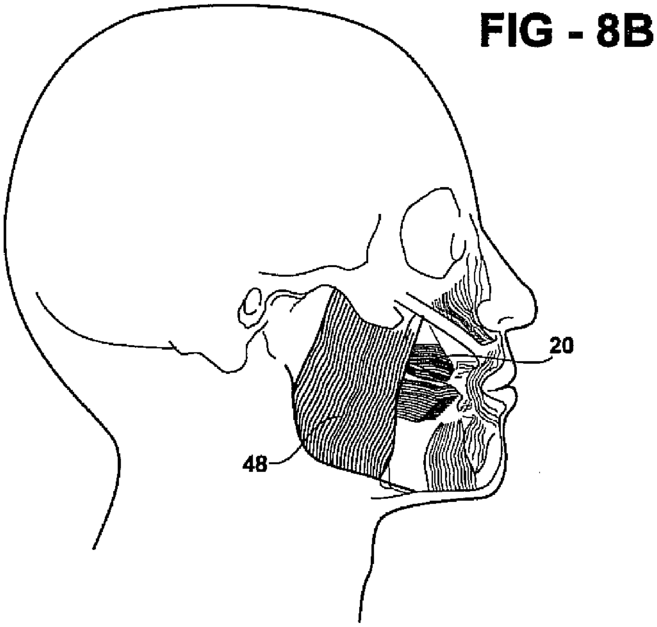
FIG. 8B is a side view of a human head illustrating the masseter and buccinator muscles.
Figure 8C:
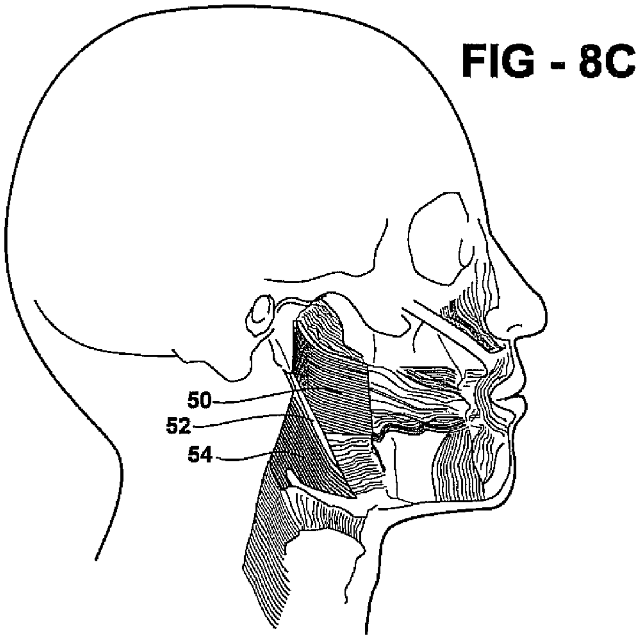
FIG. 8C is a side view of a human head illustrating the stylopharyngeus, middle pharyngeal constrictor, and superior pharyngeal constrictor muscles.
Figure 8D:
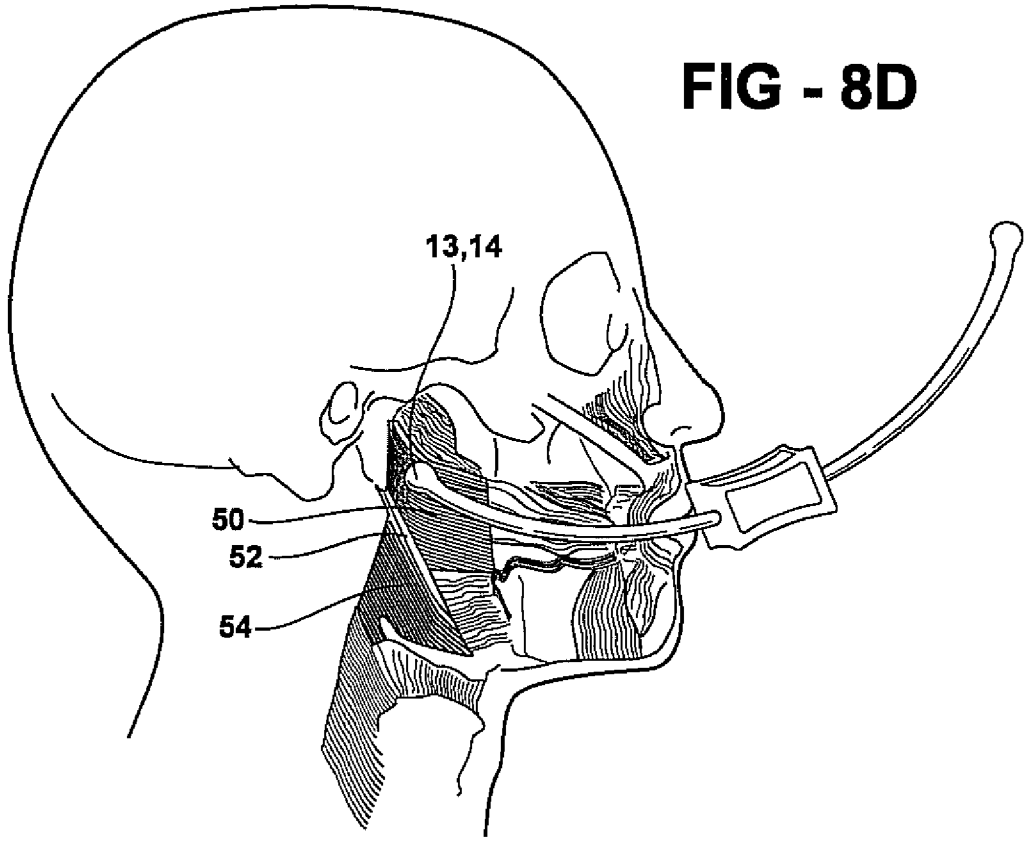
FIG. 8D is a side view similar to FIG. 8C with a device according to one embodiment of the present invention positioned for treatment.

FIG. 8 illustrates a method according to a further aspect of the present invention for achieving release and relief of intra oral muscular spasms, trigger points, and myofacial dysfunction, specifically in the area around and within the masseter 48, buccinator 20, stylopharyngeus 52, middle pharyngeal constrictor 54, and superior pharyngeal constrictor 50 muscles, shown in FIG. 8B, FIG. 8C, and FIG. 8D. As with the prior methods, the subject should start with a slightly parted, relaxed mouth and two rows of teeth inside the mouth also should be slightly apart, up to about one half of one inch. The subject can receive treatment sitting in an upright position, but it is preferred that the subject is positioned in a reclined position to 45 degrees with the head resting on some type of support, such as a head rest in a dental chair or on a pillow. Treatment can begin on either side of the mouth. When treatment of one side concludes, the user should begin treatment of the other side. The gripping portion 10 should be held such that the device is positioned generally in a horizontal plane, as shown in FIG. 8. The midportion of the elongated arm should curve toward the mouth as the device is held in a horizontal position. Stated another way, the inside of the curve of the device will be directed toward the opposite side of the head. The gripping portion will end up positioned generally in front of the mouth. The user should guide either tip of the device into the highest area of the cheek pouch 42, closest to the ear, as shown in FIG. 8. The user should locate the first area of tenderness and place the tip so that it makes contact with the area 42. The user should begin to apply pressure by pushing the tip 13, 14 toward the back of the head. For maximum benefit, the operator of the device may place his or her thumb 44 of the opposite hand on the outside of the cheek just above the ear, and apply pressure with the thumb 44. It is preferred for the operator to also commence horizontal stroking movements 46 with the thumb 44, across the device. The stroking movements 46 begin by the ear and move horizontally across the cheek toward the mouth, shown in FIG. 8. The application of pressure is the same as discussed previously. Once release and relief is achieved for one treatment point, the user should move to the next area of tenderness. For this method, to move to the next area of tenderness, the user should externally rotate the device a few degrees as shown in FIG. 8A. The degree of rotation is dependant upon the location of the next trigger or treatment point. As the device is being externally rotated, the user should also drop the placement of tip 13, 14 in order to find the next trigger or treatment point. The amount of drop is also dependant on the trigger or treatment point. It might be as close as two millimeters. For maximum benefit, the user of the device may place his or her thumb 44 of the opposite hand on the outside of the cheek at the same height as the device, and apply pressure with the thumb 44. It is preferred for the user to also commence horizontal stroking movements 46 with the thumb 44, across the tip 13, 14. The stroking movements 46 begin at the point farthest from the mouth and move horizontally across the cheek toward the mouth. The user should repeat the dropping and external rotation of the device until the user of the device has treated all of the trigger or treatment points located in the rear curve of the cheek pouch, all the way down toward the jaw. The operator of the device may find the curvature of the device ends in a position where the gripping portion points upward and the tips 13, 14 point down. The device will move from a vertical position with tips 13, 14 pointing up through a horizontal position with tips 13, 14 pointing away from the cheek and end in a vertical position with the tips 13, 14 pointing down. Those on the receiving end of treatment may find variations in preference with regard to tip selection per area of tenderness per application of sustained pressure. It is highly important for those on the receiving end of treatment to maintain an even, steady breathing pattern and to stay as relaxed as possible during treatment.

Figure 9:
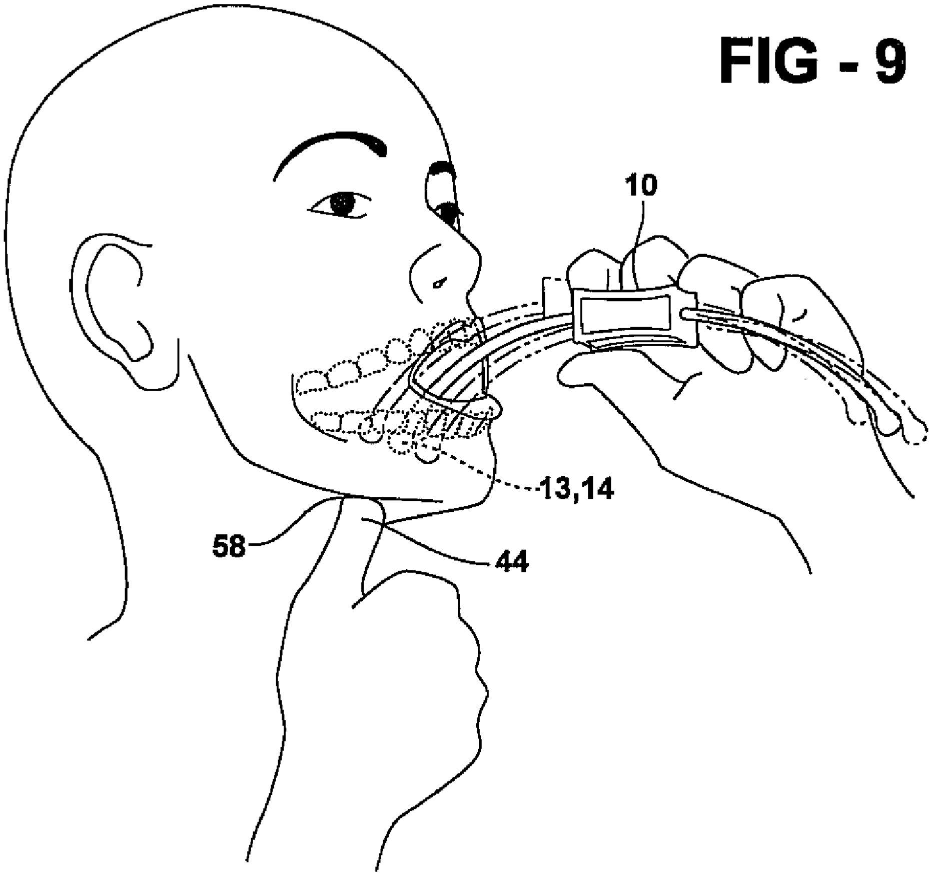
FIG. 9 is perspective view of a human head illustrating a method according to yet another aspect of the present invention for achieving release and relief of intra oral muscular spasms, trigger points, and myofacial dysfunction specifically in the area around and within the digastric, mylohyoid, geniohyoid, styloglossus, genioglossus, hyoglossus, stylohyoid, and platysma muscles.
Figure 9A:
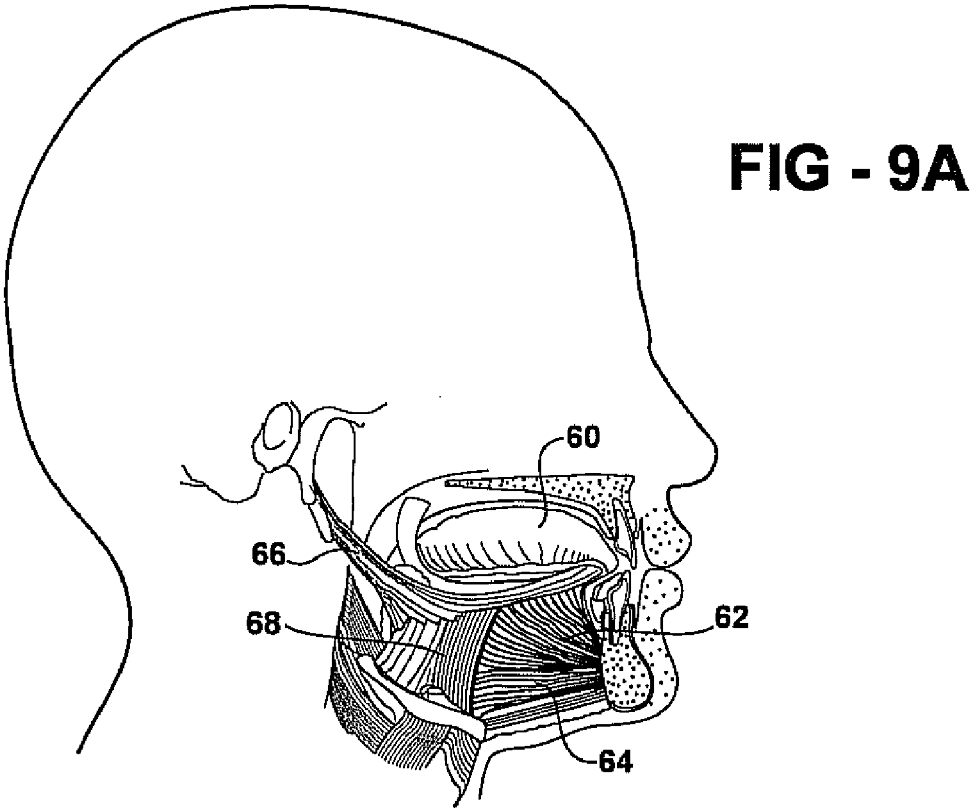
FIG. 9A is a side view of a human head illustrating the geniohyoid, styloglossus, genioglossus, and hyoglossus muscles.
Figure 9B:
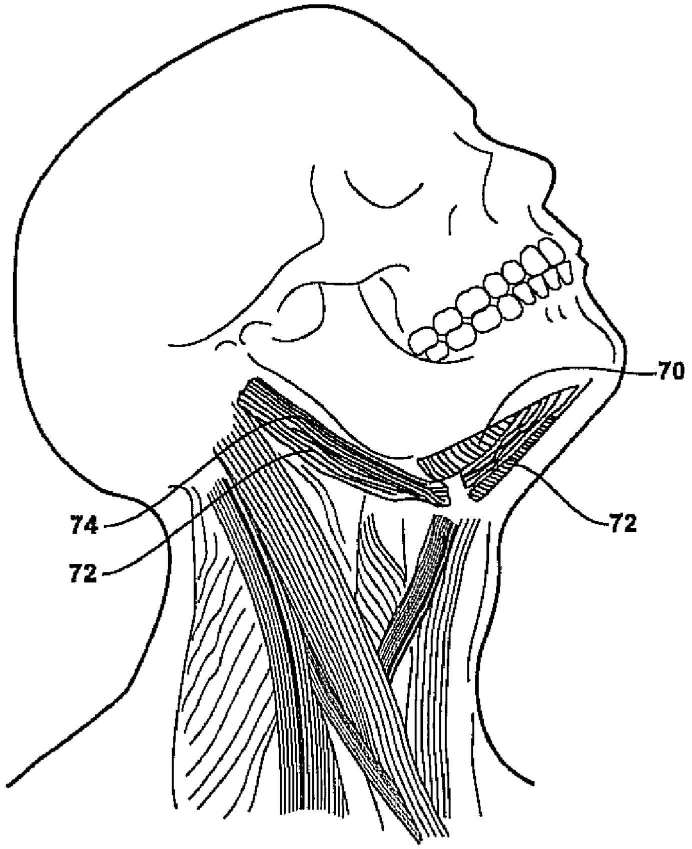
FIG. 9B is a side view of a human head illustrating the digastric, mylohyoid and stylohyoid muscles.
Figure 9C:
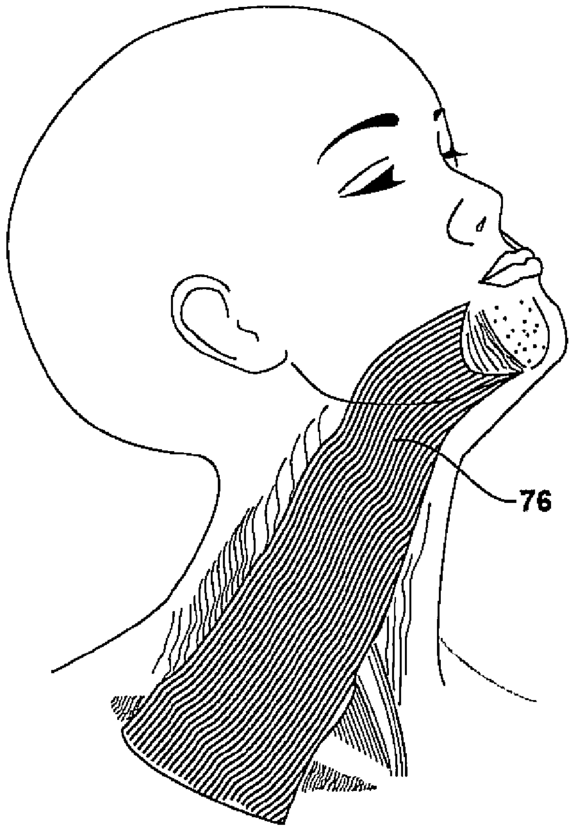
FIG. 9C is a side view of a human head illustrating the platysma muscle.
Figure 9D:
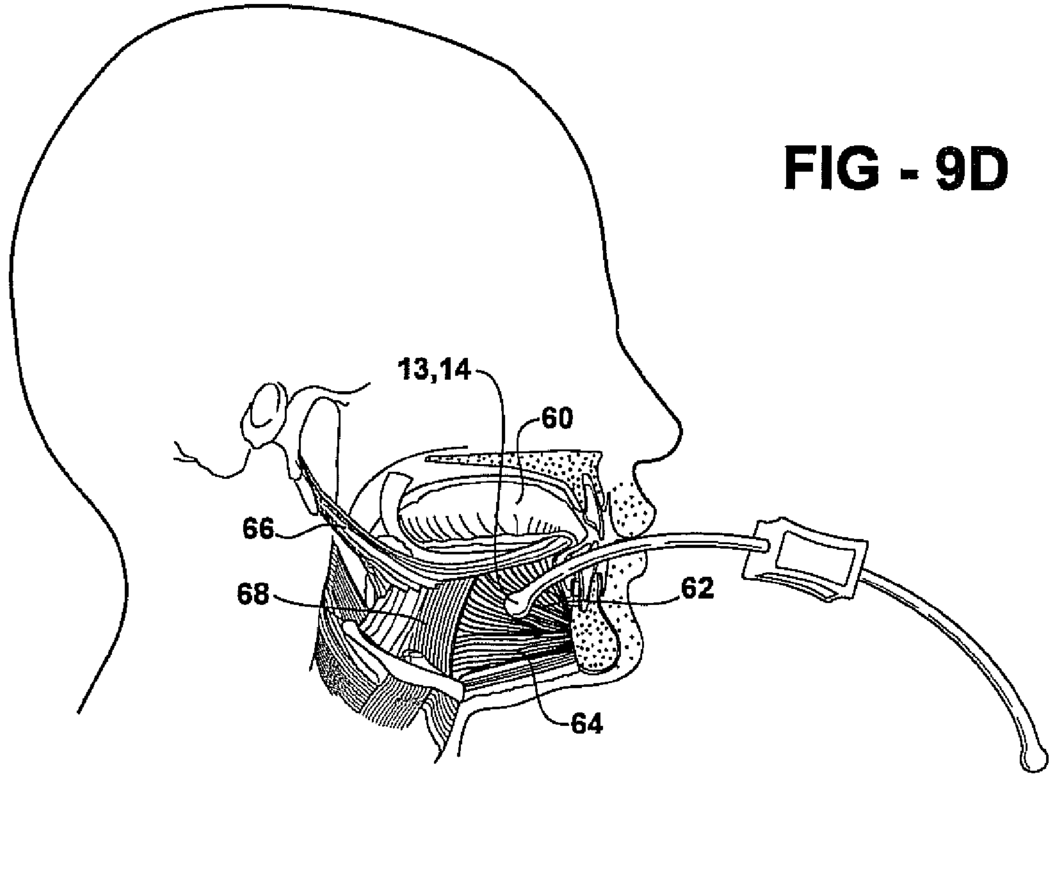
FIG. 9D is a side view similar to FIG. 9A with a device according to one embodiment of the present invention positioned for treatment.

FIG. 9 illustrates a method according to yet another aspect of the present invention for achieving release and relief of intra oral muscular spasms, trigger points, and myofacial dysfunction, specifically in the area around and within the digastric 72, mylohyoid 70, geniohyoid 64, styloglossus 66, genioglossus 62, stylohyoid 74, hyoglossus 68, and platysma 76 muscles, shown in FIG. 9A, FIG. 9B, FIG. 9C, and FIG. 9D. As with the prior methods, the subject should start with a slightly parted, relaxed mouth and two rows of teeth inside the mouth also should be slightly apart, up to about one half of one inch. The mouth can be opened wider than one half of one inch if those on the receiving end of treatment wish to do so. The subject can receive treatment sitting in an upright position, but it is preferred that the subject is positioned in a reclined position to 45 degrees with the head resting on some type of support, such as a head rest in a dental chair or on a pillow. Treatment can begin on either side of the mouth. The gripping portion 10 is held such that the device is positioned generally in a vertical plane, as shown in FIG. 9. The midportion of the elongated arm should point up so that the tips are pointing down. The user should guide either tip of the device into the area underneath the tongue 60, as shown in FIG. 9 and FIG. 9D. The user should start in the area closest to the back of the mouth, under the tongue 60 and closest to the teeth. The user should locate the first area of tenderness and place the tip 13, 14 so that it makes contact with the area. The user should begin to apply pressure by pushing the tip straight down. For maximum benefit, the operator of the device may place his or her thumb 44 of the free hand on the underside of the jaw 58 directly opposite the tip, and apply pressure with the thumb 44 at the same time the device applies pressure by pushing the thumb 44 straight up, as shown in FIG. 9. Pressure is applied as described previously. When treatment of one area concludes, the user should find the next trigger or treatment point by locating additional areas of tenderness. The user should locate and treat all areas of tenderness underneath the tongue 60. Those on the receiving end of treatment may find variations in preference with regard to tip selection per area of tenderness per application of sustained pressure. It is highly important for those on the receiving end of treatment to maintain an even, steady breathing pattern and to stay as relaxed as possible during treatment.

The foregoing description of the present invention has been presented for purposes of illustration and description. Furthermore, the description is not intended to limit the invention to the form disclosed herein. Consequently, variations and modifications commensurate with the above teaching, and the skill or knowledge of the relevant art, are within the scope of the present invention. The embodiment described hereinabove is further intended to explain the best mode known for practicing the invention and to enable others skilled in the art to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Because of the complexity of the musculature within the mouth, there may be certain muscles that are treated with this method that may or may not be listed within the scope of the present invention.

What is claimed is:

1. A method for the relief of head, face and jaw pain, including Temporomandibular Joint Disorder (TMJ) by achieving the release of intra oral muscular spasms, trigger points and myofascial dysfunction comprising the steps of:

locating intra oral treatment points selected from the group consisting of locations of intra oral muscle spasms, trigger points and myofascial dysfunction, in the mouth and jaw region of a human subject;

providing a handheld device comprising;

a central gripping portion having a pair of spaced-apart ends;

a first generally arcuate arm extending from one end of the central gripping portion and terminating in a generally bulbous tip;

a second generally arcuate arm extending from the other end of the central gripping portion and terminating in a generally flattened tip;

opening the subject's mouth sufficiently to pass one of the tips into the mouth;

inserting one of the tips into the subject's mouth and bringing the tip into contact with one of the treatment points, the other of the tips being outside the subject's mouth; and directly applying pressure to the treatment point with the tip in the subject's mouth until a release response occurs.

2. The method according to claim 1, wherein the applying pressure step comprises defining a moderate discomfort level below a point at which the patient winces or tenses involuntarily and applying a pressure at or below the moderate discomfort level.

3. The method according to claim 1, wherein the applying pressure step is performed for at least 10 seconds.

4. The method according to claim 1, wherein the release response comprises softening of the treatment point.

5. The method according to claim 1, further comprising:

repositioning the handheld device;

bringing one of the tips into contact with another of the treatment points; and repeating the applying pressure step.

6. The method according to claim 1, wherein the applying pressure step further comprises rotating the tip.

7. The method according to claim 1, wherein the applying pressure step comprises applying pressure at a plurality of dissimilar angles to the treatment point.

8. The method according to claim 1, wherein the bulbous tip of the handhetd device has a radius of curvature in the range of 0.15 to 0.4 and a width in the range of 0.25 to 0.6 and the flattened tip has a width in the range of 0.2 to 0.9 inches.

9. The method according to claim 1, wherein the tips of the handheld device have different widths and different radiuses of curvature.

10. A method for the relief of bead, face and jaw pain, including Temporomandibular Joint Disorder (TMJ) by achieving the release of intra oral muscular spasms, trigger points and myofascial dysfunction comprising the steps of:

locating a plurality of intra oral treatment points selected from the group consisting of locations of intra oral muscle spasms, trigger points and myofascial dysfunction, in the mouth and jaw region of a human subject;

providing a haudheld device comprising;

a central gripping portion having a pair of spaced apart ends;

a first generally arcuate arm extending from one end of the central gripping portion and terminating in a generally bulbous tip;

a second generally arcuate arm extending from the other end of the central gripping portion and terminating in a generally flattened tip;

opening the subject's mouth sufficiently to pass one of the tips into the mouth;

inserting one of the tips into the subject's mouth, the other of the tips being outside the subject's mouth;

positioning said one of the ups in a region selected from the group consisting of:

a first region around and within the medial pierygoid and buccinator muscles in the soft tissue area between the top and bottom molars of the subject;

a second region around and within the lateral pterygoid muscle in the area behind and slightly outside of the upper molars of the subject;

a third region around and within the palatopharyngeus, tensor veli palatini, levator veli palatine, and pterygoid muscles in the roof of the mouth in the soft palate area under the sinus cavity;

a fourth region around and within the masseter, buccinator, stylopharyngeus, middle pharyngeal constrictor, and superior pharyngeal constrictor muscles in the highest area of the cheek pouch closest to the ear; and a fifth region around and within the digastric, mylohyoid, geniohyoid, styloglossus, genioglossus, stylohyoid, hyoglossus, and platysma muscles in the area underneath the tongue;

positioning the tip in contact with a treatment point in the region; and applying pressure to the treatment point with the tip until a release response occurs.

11. The method according to claim 10, further comprising the step of moving the device so as to bring one of the tips into contract with another of the plurality of treatment points on one of the regions and repeating the applying pressure step.

12. The method according to claim 10, wherein the applying pressure step is performed for at least 10 seconds.

13. The method according to claim 10, wherein the release response comprises softening of the treatment point.

14. The method according to claim 10, wherein the applying pressure step comprises applying pressure at a plurality of dissimilar angles to the treatment point.

15. The method according to claim 10, wherein the bulbous tip of the handheld device has a radius of curvature in the range of 0.15 to 0.4 and a width in the range of 0.25 to 0.6 and the flattened tip has a width in the range of 0.2 to 0.9 inches.

16. The method according to claim 10, wherein the tips of the handheld device have different widths and different radiuses of curvature.

17. A hand-held device for insertion into the mouth of a human and for use in the release and relief of muscular spasms, trigger points and myofascial dysfunction through the systematic application of pressure, comprising:

a central gripping portion having a pair of opposed ends and a plurality of gripping faces extending between the opposed ends;

a first generally arcuate arm extending from one of the opposed ends, the arm having a base joined to the one end, a tip spaced therefrom, and an elongated midportion extending generally arcuately therebetween, the tip being generally bulbous and convex with a radius of curvature between 0.15 and 0.4 inches and a width between 0.25 and 0.6 inches;

a second generally arcuate arm extending from the other of the opposed ends, the second arm having a base joined to the other end, a tip spaced therefrom, and an elongated midportion extending generally arcuately therebetween, the tip having a face that is generally flattened with a width between 0.2 and 0.9 inches; and the midportion of at least one of the arcuate arms having a radius of curvature in the range of 3 to 6 inches;

wherein the device is configured such that when one of the tips is inserted into the mouth and brought into contact with an intra oral treatment point, the other of the tips is disposed outside the mouth.

18. The handheld device according to claim 17, wherein the midportion of each of the arcuate arms has a radius of curvature in the range of 4 to 5 inches.

19. The handheld device according to claim 17, wherein a grip axis is defined axially through the gripping portion, each tip having an end face with a tip axis being defined axial through the end face, a tip angle being defined as the angle between each tip axis and the grip axis, the tip angles being in the range of 20 to 60 degrees.

20. The handheld device according to claim 19, wherein the tip angles are in the range of 35 to 45 degrees.

21. The handheld device according to claim 17, wherein the radius of curvature of the tip of the first arm is between 0.15 and 0.25 inches, the face of the tip of the second arm having a radius of curvature greater than the radius of curvature of the tip of the first arm.

22. The haudheld device according to claim 17, wherein the first and second arms are generally coplanar.

23. The handheld device according to claim 17, wherein the device has a core formed of a first material and coating covering the core, the coating enclosing the core and being formed of a second material that is softer than the first material.

24. The handheld device according to claim 17, wherein the gripping portion has 4 gripping faces and a generally square cross section, each of the gripping faces being generally concave.

25. The handheld device according to claim 17, wherein the device has a tip-to-tip length in the range of 6 to 10 inches.

26. The handheld device according to claim 25, wherein the device has a tip-to-tip length in the range of 7 to 9 inches.

27. The handheld device according to claim 17, wherein each of the arms has a base to tip length in the range of 3 to 5 inches.

28. The handheld device according to claim 17, wherein the tip of the first arm has a diameter in the range of 0.25 to 0.35 inches and the tip of the second arm has a diameter in the range to 0.45 to 0.6 inches.

29. A hand-held device for insertion into the mouth of a human and for use in the release and relief of muscular spasms, trigger points and myofascial dysfunction through the systematic application of pressure, comprising:

a central gripping portion having a pair of opposed ends and a plurality of gripping faces extending between the opposed ends;

a first generally arcuate arm extending from one of the opposed ends and terminating in a tip; and a second generally arcuate arm extending from the other of the opposed ends and terminating in a tip;

each of the tips having a generally convex face with a width between 0.2 and 0.9 inches, the convex faces of the tips having dissimilar radiuses of curvature and different widths;

at least one of the arcuate arms has a radius of curvature in the range of 3 to 6 inches; and each of the arms having a length in the range of 3 to 5 inches.

* * * * *

UNITED STATES PATENT AND TRADEMARK OFFICE

CERTIFICATE OF CORRECTION

PATENT NO. : 7,458,377 B2
APPLICATION NO. : 10/919159
DATED : December 2, 2008
INVENTOR(S) : Gail Falzon It is certified that error appears in the above-identified patent and that said Letters Patent is hereby corrected as shown below:

Column 1, line 15, replace “myofacial” with --myofascial--
Column 1, line 18, replace “myofacial” with --myofascial--
Column 1, line 25, replace “myofacial” with --myofascial--
Column 1, line 28, replace “myofacial” with --myofascial--
Column 1, line 30, replace “myofacial” with --myofascial--
Column 1, line 33, replace “myofacial” with --myofascial--
Column 1, line 36, replace “myofacial” with --myofascial--
Column 1, line 37, replace “myofacial” with --myofascial--
Column 2, line 14, replace “myofacial” with --myofascial--
Column 2, line 21, replace “myofacial” with --myofascial--
Column 2, line 59, replace “myofacial” with --myofascial--
Column 3, line 19, replace “myofacial” with --myofascial--
Column 3, line 31, replace “myofacial” with --myofascial--
Column 3, line 42, replace “myofacial” with --myofascial--
Column 3, line 47, replace “myofacial” with --myofascial--
Column 3, line 63, replace “myofacial” with --myofascial--
Column 4, line 25, replace “myofacial” with --myofascial--
Column 4, line 36, replace “myofacial” with --myofascial--
Column 4, line 46, replace “myofacial” with --myofascial--
Column 4, line 54, replace “myofacial” with --myofascial--
Column 4, line 67, replace “myofacial” with --myofascial--
Column 5, line 17, replace “myofacial” with --myofascial--
Column 5, line 38, replace “myofacial” with --myofascial--
Column 5, line 42, replace “myofacial” with --myofascial--
Column 5, line 54, replace “myofacial” with --myofascial--

Signed and Sealed this

Twenty-first Day of April, 2009

John Doll

JOHN DOLL
*Acting Director of the United States Patent and Trademark Office*